US 8,696,593 B2

(12) United States Patent
Campbell et al.

(10) Patent No.: US 8,696,593 B2
(45) Date of Patent: Apr. 15, 2014

(54) METHOD AND SYSTEM FOR MONITORING INTRACRANIAL PRESSURE

(75) Inventors: Shannon E. Campbell, Oakland, CA (US); Clark R. Baker, Jr., Newman, CA (US)

(73) Assignee: Covidien LP, Mansfield, MA (US)

( * ) Notice: Subject to any disclaimer, the term of this patent is extended or adjusted under 35 U.S.C. 154(b) by 1853 days.

(21) Appl. No.: 11/528,218

(22) Filed: Sep. 27, 2006

(65) Prior Publication Data
US 2008/0077023 A1 Mar. 27, 2008

(51) Int. Cl.
*A61B 5/00* (2006.01)

(52) U.S. Cl.
USPC .......................................................... 600/561

(58) Field of Classification Search
USPC .................. 600/561, 585, 486, 398, 315, 331
See application file for complete search history.

(56) References Cited

U.S. PATENT DOCUMENTS

| 3,638,640 | A | | 2/1972 | Shaw |
| 4,378,809 | A | * | 4/1983 | Cosman ........................ 600/561 |
| 4,714,341 | A | | 12/1987 | Hamaguri et al. |
| 4,805,623 | A | | 2/1989 | Jöbsis |
| 4,911,167 | A | | 3/1990 | Corenman et al. |
| 4,936,679 | A | | 6/1990 | Mersch |
| 4,972,331 | A | | 11/1990 | Chance |
| 5,119,815 | A | | 6/1992 | Chance |
| 5,122,974 | A | | 6/1992 | Chance |
| 5,167,230 | A | | 12/1992 | Chance |
| 5,256,401 | A | | 10/1993 | Duckenfield et al. |
| 5,267,563 | A | | 12/1993 | Swedlow et al. |
| 5,297,548 | A | | 3/1994 | Pologe |
| 5,355,880 | A | | 10/1994 | Thomas et al. |
| 5,372,136 | A | | 12/1994 | Steuer et al. |
| 5,385,143 | A | | 1/1995 | Aoyagi |
| 5,392,777 | A | | 2/1995 | Swedlow et al. |
| 5,482,036 | A | | 1/1996 | Diab et al. |
| 5,553,614 | A | | 9/1996 | Chance |
| 5,564,417 | A | | 10/1996 | Chance |
| 5,575,285 | A | | 11/1996 | Takanashi et al. |
| 5,617,873 | A | * | 4/1997 | Yost et al. ..................... 600/561 |

(Continued)

FOREIGN PATENT DOCUMENTS

| DE | 102 13 692 A1 | 10/2003 |
| JP | 5-212016 | 8/1993 |

(Continued)

OTHER PUBLICATIONS

Jacks et al, Spontaneous Retinal Venous Pulsation: Aetiology and Significance, Jul. 24, 2002, Journal of Neurology, Neurosurgery and Psychiatry, 74, 1, p. 7-9.*

(Continued)

*Primary Examiner* — Brian Szmal
*Assistant Examiner* — H. Q. Nguyen
(74) *Attorney, Agent, or Firm* — Fletcher Yoder

(57) ABSTRACT

Embodiments of the present invention relate to a system and method for monitoring intracranial pressure. Embodiments of the present invention include emitting an electromagnetic wavelength into forehead tissue of a patient and detecting characteristics of the electromagnetic wavelength after the electromagnetic wavelength has been scattered by the tissue. The characteristics may include variations in the electromagnetic wavelength corresponding to a pulse. Further, embodiments of the present invention include analyzing the variations to identify venous pulsations, and determining whether intracranial pressure is elevated in the patient based on a correlation between the venous pulsations and levels of intracranial pressure.

18 Claims, 4 Drawing Sheets

(56) References Cited

U.S. PATENT DOCUMENTS

| | | | |
|---|---|---|---|
| 5,630,413 A | 5/1997 | Thomas et al. | |
| 5,645,059 A | 7/1997 | Fein et al. | |
| 5,645,060 A | 7/1997 | Yorkey | |
| 5,692,503 A | 12/1997 | Keunstner | |
| 5,758,644 A | 6/1998 | Diab et al. | |
| 5,779,631 A | 7/1998 | Chance | |
| 5,830,139 A | 11/1998 | Abreu | |
| 5,842,981 A | 12/1998 | Larsen et al. | |
| 5,873,821 A | 2/1999 | Chance et al. | |
| 5,995,856 A | 11/1999 | Mannheimer et al. | |
| 6,011,986 A | 1/2000 | Diab et al. | |
| 6,064,898 A | 5/2000 | Aldrich | |
| 6,120,460 A | 9/2000 | Abreu | |
| 6,134,460 A | 10/2000 | Chance | |
| 6,163,715 A | 12/2000 | Larsen et al. | |
| 6,181,958 B1 | 1/2001 | Steuer et al. | |
| 6,230,035 B1 | 5/2001 | Aoyagi et al. | |
| 6,266,546 B1 | 7/2001 | Steuer et al. | |
| 6,312,393 B1 | 11/2001 | Abreu | |
| 6,350,460 B1 | 2/2002 | Andrews et al. | |
| 6,397,091 B2 | 5/2002 | Diab et al. | |
| 6,415,236 B2 | 7/2002 | Kobayashi et al. | |
| 6,438,399 B1 | 8/2002 | Kurth | |
| 6,487,439 B1 | 11/2002 | Skladnev et al. | |
| 6,491,647 B1 * | 12/2002 | Bridger et al. | 600/585 |
| 6,501,974 B2 | 12/2002 | Huiku | |
| 6,501,975 B2 | 12/2002 | Diab et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,591,122 B2 | 7/2003 | Schmitt | |
| 6,594,513 B1 | 7/2003 | Jobsis et al. | |
| 6,606,509 B2 | 8/2003 | Schmitt | |
| 6,615,064 B1 | 9/2003 | Aldrich | |
| 6,622,095 B2 | 9/2003 | Kobayashi et al. | |
| 6,658,277 B2 | 12/2003 | Wasserman | |
| 6,662,030 B2 | 12/2003 | Khalil et al. | |
| 6,671,526 B1 | 12/2003 | Aoyagi et al. | |
| 6,671,528 B2 | 12/2003 | Steuer et al. | |
| 6,675,031 B1 | 1/2004 | Porges et al. | |
| 6,678,543 B2 | 1/2004 | Diab et al. | |
| 6,690,958 B1 | 2/2004 | Walker et al. | |
| 6,708,048 B1 | 3/2004 | Chance | |
| 6,711,424 B1 | 3/2004 | Fine et al. | |
| 6,711,425 B1 | 3/2004 | Reuss | |
| 6,748,254 B2 | 6/2004 | O'Neil et al. | |
| 6,773,407 B2 * | 8/2004 | Yost et al. | 600/561 |
| 6,785,568 B2 | 8/2004 | Chance | |
| 6,801,797 B2 | 10/2004 | Mannheimer et al. | |
| 6,801,799 B2 | 10/2004 | Mendelson | |
| 6,811,538 B2 | 11/2004 | Westbrook et al. | |
| 6,832,113 B2 | 12/2004 | Belalcazar | |
| 6,873,865 B2 | 3/2005 | Steuer et al. | |
| 6,934,570 B2 | 8/2005 | Kiani et al. | |
| 6,934,571 B2 | 8/2005 | Wiesmann et al. | |
| 6,947,781 B2 | 9/2005 | Asada et al. | |
| 6,949,081 B1 | 9/2005 | Chance | |
| 6,961,598 B2 | 11/2005 | Diab | |
| 6,985,763 B2 | 1/2006 | Boas et al. | |
| 7,027,849 B2 | 4/2006 | Al-Ali | |
| 7,047,056 B2 | 5/2006 | Hannula et al. | |
| 7,072,701 B2 | 7/2006 | Chen et al. | |
| 7,215,991 B2 | 5/2007 | Besson et al. | |
| 7,221,969 B2 | 5/2007 | Stoddart et al. | |
| 7,263,395 B2 | 8/2007 | Chan et al. | |
| 7,289,837 B2 | 10/2007 | Mannheimer et al. | |
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |
| 2001/0044700 A1 | 11/2001 | Kobayashi et al. | |
| 2002/0026106 A1 | 2/2002 | Khalil et al. | |
| 2002/0035318 A1 | 3/2002 | Mannheimer et al. | |
| 2002/0038079 A1 | 3/2002 | Steuer et al. | |
| 2002/0042558 A1 | 4/2002 | Mendelson | |
| 2002/0049389 A1 | 4/2002 | Abreu | |
| 2002/0062071 A1 | 5/2002 | Diab et al. | |
| 2002/0111748 A1 | 8/2002 | Kobayashi et al. | |
| 2002/0133068 A1 | 9/2002 | Huiku | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0198443 A1 | 12/2002 | Ting | |
| 2003/0023140 A1 | 1/2003 | Chance | |
| 2003/0055324 A1 | 3/2003 | Wasserman | |
| 2003/0060693 A1 | 3/2003 | Monfre et al. | |
| 2003/0139687 A1 | 7/2003 | Abreu | |
| 2003/0144584 A1 | 7/2003 | Mendelson | |
| 2003/0220548 A1 | 11/2003 | Schmitt | |
| 2003/0220576 A1 | 11/2003 | Diab | |
| 2004/0010188 A1 | 1/2004 | Wasserman | |
| 2004/0054270 A1 | 3/2004 | Pewzner et al. | |
| 2004/0087846 A1 | 5/2004 | Wasserman | |
| 2004/0107065 A1 | 6/2004 | Al-Ali | |
| 2004/0127779 A1 | 7/2004 | Steuer et al. | |
| 2004/0171920 A1 | 9/2004 | Mannheimer et al. | |
| 2004/0176670 A1 | 9/2004 | Takamura et al. | |
| 2004/0176671 A1 | 9/2004 | Fine et al. | |
| 2004/0230106 A1 | 11/2004 | Schmitt et al. | |
| 2004/0230124 A1 * | 11/2004 | Querfurth | 600/485 |
| 2005/0059869 A1 | 3/2005 | Scharf et al. | |
| 2005/0080323 A1 | 4/2005 | Kato | |
| 2005/0101850 A1 | 5/2005 | Parker | |
| 2005/0107676 A1 | 5/2005 | Acosta et al. | |
| 2005/0113656 A1 | 5/2005 | Chance | |
| 2005/0168722 A1 | 8/2005 | Forstner et al. | |
| 2005/0192488 A1 | 9/2005 | Bryenton et al. | |
| 2005/0197579 A1 * | 9/2005 | Baker, Jr. | 600/473 |
| 2005/0203357 A1 | 9/2005 | Debreczeny et al. | |
| 2005/0267346 A1 | 12/2005 | Faber et al. | |
| 2005/0277819 A1 | 12/2005 | Kiani et al. | |
| 2005/0283082 A1 | 12/2005 | Geddes et al. | |
| 2006/0009688 A1 | 1/2006 | Lamego et al. | |
| 2006/0015021 A1 | 1/2006 | Cheng | |
| 2006/0020181 A1 | 1/2006 | Schmitt | |
| 2006/0030763 A1 | 2/2006 | Mannheimer et al. | |
| 2006/0052680 A1 | 3/2006 | Diab | |
| 2006/0058683 A1 | 3/2006 | Chance | |
| 2006/0074283 A1 * | 4/2006 | Henderson et al. | 600/315 |
| 2006/0189861 A1 | 8/2006 | Chen et al. | |
| 2006/0195028 A1 | 8/2006 | Hannula et al. | |
| 2006/0224053 A1 | 10/2006 | Black et al. | |
| 2006/0253007 A1 | 11/2006 | Cheng et al. | |
| 2006/0264722 A1 | 11/2006 | Hannula et al. | |
| 2006/0264723 A1 | 11/2006 | Hannula et al. | |
| 2006/0264724 A1 | 11/2006 | Hannula et al. | |
| 2006/0264725 A1 | 11/2006 | Hannula et al. | |
| 2006/0264727 A1 | 11/2006 | Mannheimer et al. | |
| 2006/0281984 A1 | 12/2006 | Mannheimer et al. | |
| 2006/0287590 A1 * | 12/2006 | McEowen | 600/331 |

FOREIGN PATENT DOCUMENTS

| | | |
|---|---|---|
| JP | 3635331 | 4/2005 |
| JP | 25095465 | 4/2005 |
| JP | 26075354 | 3/2006 |
| JP | 26122458 | 5/2006 |
| JP | 3797454 | 7/2006 |
| JP | 26201114 | 8/2006 |
| JP | 26239267 | 9/2006 |
| JP | 26297125 | 11/2006 |
| JP | 26325766 | 12/2006 |
| JP | 26326153 | 12/2006 |
| JP | 3944448 | 7/2007 |
| WO | WO 92/20273 | 11/1992 |
| WO | WO 94/03102 | 2/1994 |
| WO | WO 97/49330 | 12/1997 |
| WO | WO 01/45553 A1 | 6/2001 |

(56) References Cited

FOREIGN PATENT DOCUMENTS

| WO | WO 2007/117570 A2 * | 10/2007 | ............. B01D 59/44 |
| WO | 2008004205 | 1/2008 | |

OTHER PUBLICATIONS

Lee, Jason C.S., et al., "Measurement of Percent Carboxyhemoglobin with Pulse-Oximetry Technique," *IEEE Engineering in Medicine & Biology Society 10th Annual International Conference*, CH2566-8, vol. 88, pp. 1781-1782 (1988).

Lee, Jason C.S., et al., "Simultaneous Measurement of Percent Carboxyhemoglobin and Functional Oxygen Saturation," *IEEE Engineering in Medicine and Biology Society*, CH2770-6, vol. 89, pp. 1092-1093.

Bongard, Frederic S., et al., "Continuous Dual Oximetry in Surgical Critical Care—Indications and Limitations," *Annals of Surgery*, vol. 216, No. 1, pp. 60-68 (Jul. 1992).

Tekscan, "Medical Pressure Measurement Overview", Copyright 2006, printed Mar. 2, 2006, (2 pages), http://www.tekscan.com/medical.html.

Tekscan, "Medical Pressure Mapping Applications & Case Studies", Copyright 2006, printed Mar. 2, 2006, (1 page), http://www.tekscan.com/medical/applications.html.

Tekscan, "The Vascular/Garment (VG) System", Copyright 2006, printed Mar. 2, 2006, (1 page), http://www.tekscan.com/medical/system_vascular.html.

Tekscan, "Medical Pressure Mapping System Descriptions", Copyright 2006, printed Mar. 2, 2006, (4 pages), http://www.tekscan.com/medical/systems.html.

Tekscan, "Medical Sensor Catalog", Copyright 2006, printed Mar. 2, 2006, (3 pages), http://www.tekscan.com/medical/catalog.html.

Global Spec, "I-Scan Handheld System", Copyright 1999-2006, printed Mar. 2, 2006, (1 page), http://www.globalspec.com/FeaturedProducts/Detail/Tekscan/IScan_Handheld_System_/24720/1.

Global Spec, "The I-Scan System", Copyright 1999-2006, printed Mar. 2, 2006, (1page), http://www.globalspec.com/Featured_Products/Detail/Tekscan/The_IScan_System/5012/1.

Global Spec, "Custom FlexiForce Sensors", Copyright 1999-2006, printed Mar. 2, 2006, (1 page), http://www.globalspec.com/FeaturedProducts/Detail/Tekscan/Custom_FlexiForce_Sensors/18353/1.

Nuffield Dept. of Anesthetics University of Oxford, "Intracranial Pressure and Cerebral Blood Flow", Copyright 2006, printed Mar. 9, 2006, (10 pages), http://www.nda.ox.ac.uk/wfsa/html/u08/u08_013.htm.

Dr. A. Vincent Thamburaj, "Neurosurgery on the Web, Intracranial Pressure", printed Mar. 9, 2006, (6 pages), http://www.thamburagj.com/intracranial_pressure.htm.

Michael W. Russell, MD, Anesthesia Patient Safety Foundation, "Another Look at the Forehead Sensor", Copyright 2006, printed Mar. 13, 2006, (3 pages), http://www.apsf.org/resource_center/newsletter/2004/fall/03forehead.htm.

PicuBook, "Intracranial Pressure/Head Elevation", printed Mar. 2, 2006, (2 pages), http://pedsccm.wust1.edu/All-Net/english/neurpage/protect/icp-tx-3.htm.

Patient UK, "Rising Intracranial Pressure—Signs and Actions", Copyright 1997-2006, printed Mar. 2, 2006, (3 pages), http://www.patient.co.uk/showdoc/40001329/.

The University of Adelaide Australia, "Intracranial Pressure", Copyright 2005, printed Mar. 2, 2006, (6 pages), http://www.health.adelaide.edu.au/paed-neuro/pressure.html.

Medline Plus, "Increased Intracranial Pressure", printed Mar. 2, 2006, (3 pages), http://www.nlm.nih.gov/medlineplus/ency/article/000793,htm.

Medline Plus, "Intracranial Pressure Monitoring", printed Mar. 2, 2006, (3 pages), http://www.nlm.nih.gov/medlineplus/ency/article/003411.htm.

* cited by examiner

METHOD AND SYSTEM FOR MONITORING INTRACRANIAL PRESSURE

BACKGROUND OF THE INVENTION

1. Field of the Invention

The present invention relates generally to a method and system for detecting elevated intracranial pressure. Specifically, embodiments of the present invention relate to using venous pulsation signals obtained from a patient's forehead to non-invasively detect elevated intracranial pressure. Further, some embodiments are directed to quantifying intracranial pressure based on a pressure or elevation required to overcome the venous pulsations.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

The human skull is essentially a rigid fluid-filled container. Principle constituents within the skull include brain tissue, blood, and cerebral-spinal fluid (CSF). Because the skull is essentially rigid and has a constant volume, if there is an increase in the volume of the contents of the skull, the pressure inside the skull (i.e., intracranial pressure) will rise unless some fluid is able to escape. For example, if the brain tissue experiences swelling, a certain amount of blood or CSF must escape the skull cavity to prevent a rapid increase in pressure. During such swelling, pressure inside the skull may rise above the normal range. Further, if swelling continues until little or no fluid remains, any further swelling will cause a rapid increase in intracranial pressure (ICP). It should also be noted that obstruction of fluid flow out of the skull (e.g., obstructed venous outflow) can increase ICP because the fluid flowing into the skull will build pressure therein.

ICP is measured in millimeters of mercury (mmHg). The normal range for ICP values is from around 5 mmHg to around 13 mmHg. American and European head injury guidelines recommend that actions be taken to treat ICP when it is above 20-25 mmHg, as elevated ICP is a potentially life-threatening condition. Treatment of elevated ICP typically begins with administration of drugs to reduce systemic fluid volume or blood pressure. If the elevated ICP is not detected early enough, part of the skull may need to be removed to relieve the pressure.

While elevated ICP is often a result of trauma, the elevated pressure itself can cause damage to the central nervous system by compressing important brain structures and restricting blood flow through vessels that supply the brain. Elevated ICP typically occurs as a result of increased volume within the skull cavity. For example, elevated ICP occurs acutely in head trauma cases involving cerebral edema, which is also referred to as brain swelling. Elevated ICP may occur more gradually in cases of hydroencephalitis (i.e., water on the brain) or brain tumors. Other conditions that may cause elevated ICP include: subdural hematoma, encephalitis, meningitis, hemorrhage, stroke, and so forth.

Traditional techniques for monitoring and measuring ICP generally involve the use of invasive devices. For example, commonly used devices include hollow screw and bolt devices. These typically include metallic cylindrical instruments which are inserted into the patient such that an instrument tip protrudes into the subarachnoid space to facilitate pressure measurement. The subarachnoid space is the compartment within the skull and spinal column that contains the CSF. Another commonly used invasive device for ICP monitoring is an intraventricular catheter. The intraventricular catheter is typically placed inside ventricles (i.e., fluid filled cavities) of the brain to facilitate pressure monitoring. Insertion of such invasive devices (e.g., hollow screws and catheters) to facilitate ICP monitoring can be dangerous. For example, insertion of a monitoring device through a patient's skull may cause hemorrhaging or infection.

Some existing techniques for monitoring ICP are non-invasive. For example, some existing methods involve emitting ultrasound into the patient's brain to facilitate detection of an elevated ICP. Such utlrasound emissions typically reach the brain through natural windows in the skull. For example, ultrasound emissions may be introduced to a patient's brain via an eye socket. However, these ultrasound emissions may be undesirable depending on how long the eye must be esonified. Further, sensor placement for such methods can be difficult, resulting in inaccuracies.

Accordingly, it is desirable to provide an improved non-invasive monitoring device for detecting and/or measuring ICP that facilitates early detection of elevated ICP.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Embodiments of the present invention relate to using venous pulsation signals obtained from veins in a patient's forehead via a pulse detection sensor (e.g., a pulse oximeter sensor) to non-invasively detect and/or measure elevated intracranial pressure (ICP). For example, in some embodiments, a counter-pressure may be applied to the veins in a patient's forehead to cause cessation of the venous pulses, and the measured counter-pressure may be directly correlated to ICP. In other embodiments, the natural cessation of venous pulsations may be detected, which may be indicative of elevated ICP. Further, it is predicted that certain aspects of the venous pulsations will correlate directly with ICP. Accordingly, embodiments of the present invention include measuring venous pulsations in a patient's forehead and identifying and/or quantifying ICP using predicted correlations between the venous pulsations and ICP.

In some embodiments, measured adjustments (e.g., application of pressure or elevation of a patient's head) may be applied to the patient to stop detected venous pulsations. For example, in one embodiment, a measured amount of pressure may be applied to the forehead to stop the venous pulsations. Because venous blood in the forehead is in direct communication with that of the brain, the pressure required to abolish the venous pulsations will likely be equivalent to the maximum pressure in the brain, up to approximately 25 mmHg when the "window" for venous outflow become occluded. Similarly, in another embodiment, the patient's head may be elevated above the patient's heart until the venous pulsations cease. It is believed that the elevation required to stop the venous pulsations will correlate to ICP. Accordingly, the level of elevation may be measured and used to estimate ICP. For example, constant gravitational forces combined with the angle of elevation may be used in an algorithm to establish a value for ICP.

Figure 1:
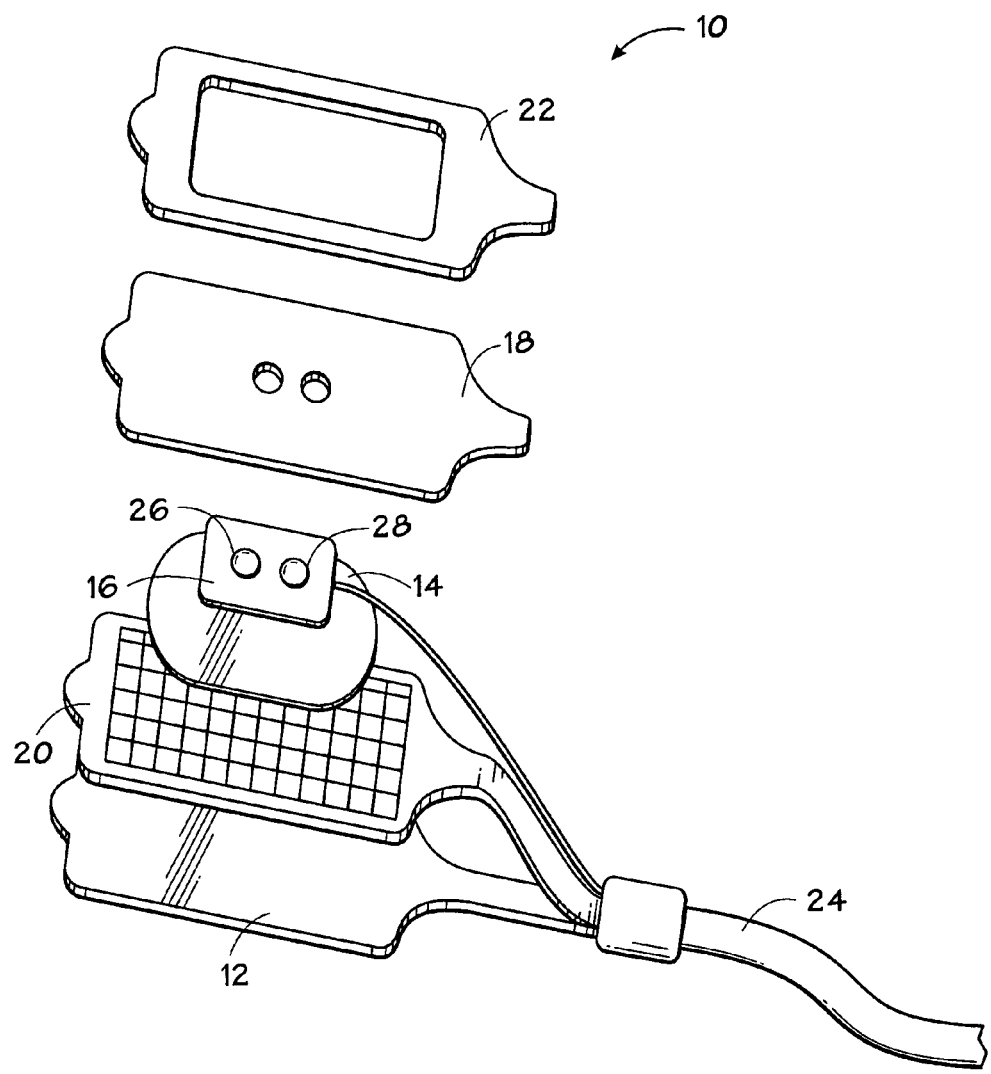
FIG. 1 is an exploded perspective view of an exemplary forehead sensor configured to detect venous pulsations and facilitate estimation of intracranial pressure levels in accordance with an exemplary embodiment of the present invention.

FIG. 1 is an exploded perspective view of a forehead sensor in accordance with an exemplary embodiment of the present invention. The sensor is generally indicated by reference number 10. In the illustrated embodiment, the sensor 10 includes a cover 12, a first mask layer 14, an optical measurement device 16, a second mask layer 18, a pressure sheet 20, and an adhesive layer 22. The sensor 10 may be coupled to a cord 24 to enable communication between components of the sensor 10 (e.g., the optical measurement device 16 and the pressure sheet 20) and a monitor (e.g., pulse oximeter and/or pressure mapping system). The cord 24 may also supply power to the sensor 10. In other embodiments, the sensor 10 may be powered by a battery and communicate wirelessly with the monitor.

The cover 12 serves as a protective outer layer for the sensor 10 and is exposed to the environment when the sensor 10 is attached to a patient's skin. The cover 12 may be made of polyvinyl chloride (PVC) foam, urethane foam material, or the like. The cover 12 at least partially covers and protects the optical measurement device 16, which includes an emitter 26 and a detector 28. In one embodiment, the emitter 26 is configured to generate light (or electromagnetic energy) of at least two different wavelengths and the detector 28 is configured to detect the generated light (or electromagnetic energy). The sensor 10 is configured such that light from the emitter 26 can be directed at a patient's skin and scattered through the patient's tissue. The amount of light that diffuses through the patient's tissue will vary in accordance with the amount of blood constituent in the tissue and the corresponding light absorption. Accordingly, the amount of light detected by the detector 28 can be utilized to measure certain blood flow characteristics, such as venous pulsations.

The first and second mask layers 14 and 18 (e.g., metalized plastic film) are positioned on either side of the optical measurement device 16 to reduce or prevent secondary light (i.e., light other than that produced by the emitter 26) from interfering with the detector 18. To allow optical access to the patient, the first and second mask layers 14 and 18 do not completely cover the optical measurement device 16. For example, the second mask layer 18 has openings therein that fit over and surround portions of the optical measurement device 16 such that light can be emitted into the patient's tissue by the emitter 26 and detected by the detector 28. In one embodiment, the first and second mask layers 14 and 18 are made of a cellular urethane foam and couple to other portions of the sensor 10 with a pressure sensitive adhesive. Either of the mask layers 14 or 18 may serve as a substantially flat platform for attachment of the pressure sheet 20 and/or the adhesive layer 22.

The pressure sheet 20 is configured to work with a pressure mapping system to determine pressure levels on portions of the sheet 20. Specifically, the pressure sheet 20 may be used to measure or detect certain levels of patient/surface interface pressure. For example, the pressure sheet 20 may measure pressure applied to the patient's forehead by a clinician pressing on the sensor 10. The pressure sheet 20 may include any pressure sensing device adapted to measure dynamic and/or static pressure distribution. For example, the pressure sheet 20 may include certain pressure measurement devices provided by Tekscan, Inc. In one embodiment, the pressure sheet 20 may include a tactile sensing system that provides an essentially instantaneous assessment of topical pressure being applied to the pressure sheet 20. The pressure measured by the pressure sheet 20 may be utilized in a calculation to determine the ICP of the patient. Further, the pressure sheet 20 may communicate via an electrical connection or wirelessly with the pressure mapping system to facilitate measurement and storage of pressure data. It should be noted that in some embodiments, the pressure sheet 20 may be separate from other components of the sensor 10 or disposed on an external portion of the sensor 10.

The adhesive layer 22 is disposed on the outer portion of the sensor 10 opposite the cover 12 and is adapted to facilitate attachment of the sensor 10 to a patient. In the illustrated embodiment, the adhesive layer 22 is essentially ring shaped with an opening to facilitate optical communication between the optical measurement device 16 and the patient's tissue. The adhesive layer 22 may be dark (e.g., black) to reduce reflected light, which can impact measurement accuracy. Further, the adhesive layer 22 may include a thermally stable adhesive material to avoid compromised performance when the sensor 10 is exposed to heat. In one embodiment, the adhesive layer 22 includes a plastic strip having acrylic adhesive on one side for attachment to the patient. In another embodiment, the adhesive layer 22 includes multiple adhesive sheets.

Figure 2:
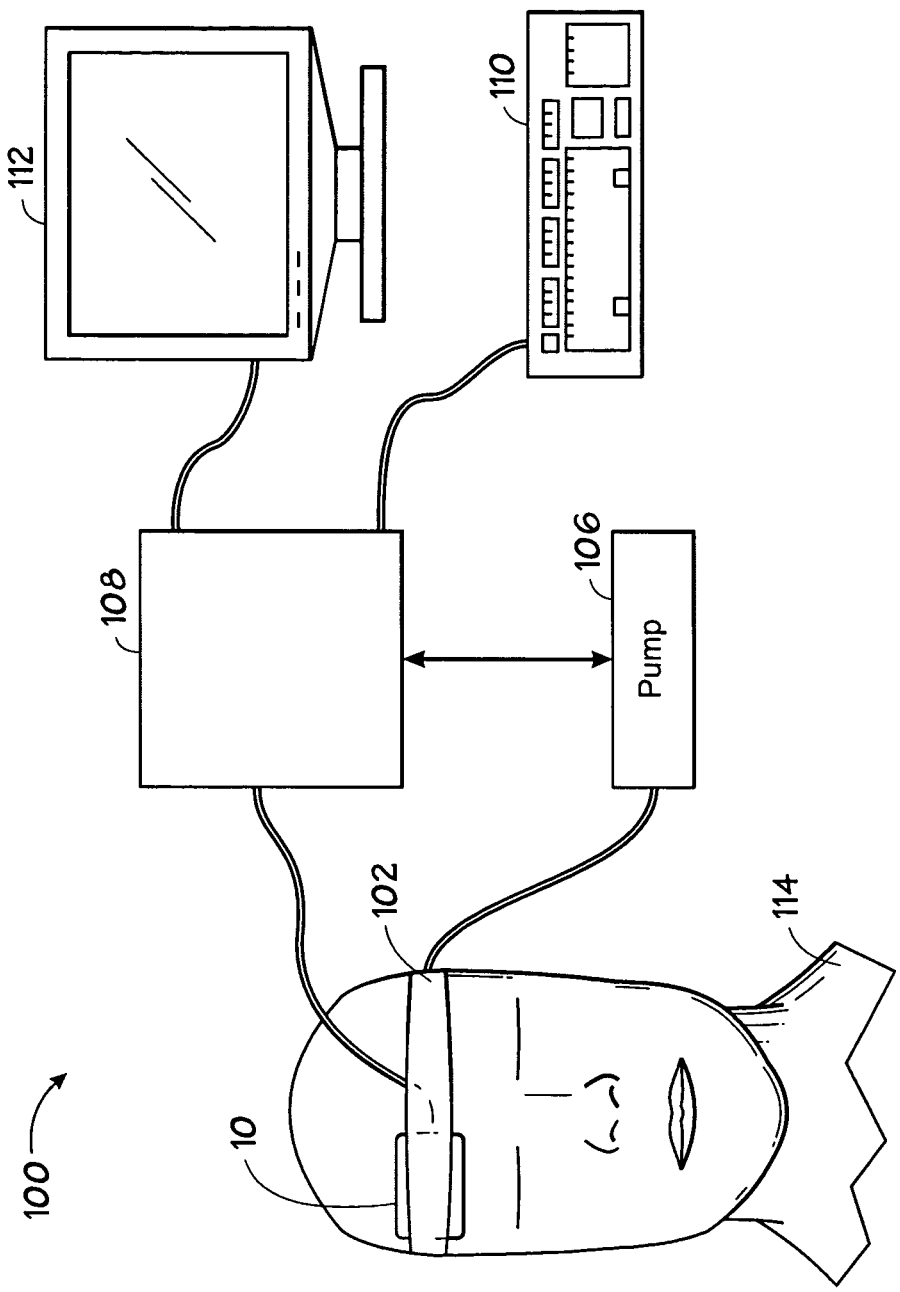
FIG. 2 is a block diagram of an exemplary system for non-invasively monitoring a patient's intracranial pressure in accordance with an exemplary embodiment of the present invention.

FIG. 2 is a block diagram of a system for non-invasively monitoring a patient's ICP in accordance with an exemplary embodiment of the present invention. The system is generally designated by reference number 100. The system 100 includes the sensor 10, an inflatable headband 102, a pump 106, a monitor 108, an input device 110, and an output screen 112. The monitor 108 may include a vital signs monitor (e.g., a pulse rate monitor, a pulse oximeter) and/or a pressure mapping device. For example, the monitor 108 may be adapted to receive input from the optical measurement device 16 of the sensor 10 relating to detecting venous pulsations. Additionally, the monitor may be adapted to receive input from the pressure sheet 20 of the sensor 10 relating to detecting an amount of pressure applied between the patient and the sensor. The monitor 108 may utilize correlations between venous pulsations and pressure measurements to facilitate estimation of ICP in accordance with embodiments of the present invention.

The system 100 is coupled to a patient 114 to allow monitoring of the patient's ICP. Specifically, the system 100 is coupled to the patient 114 via the sensor 10, which is attached to the patient's forehead and held in place by adhesive and/or the headband 102. As set forth above, the sensor 10 may be adapted to emit light into the patient's tissue and detect how the light is dispersed by the tissue to provide an estimate of certain blood flow characteristics, such as venous pulsations. This detection of venous pulsations may be achieved in accordance with known systems (e.g., pulse oximeters) and devices.

Figure 3:
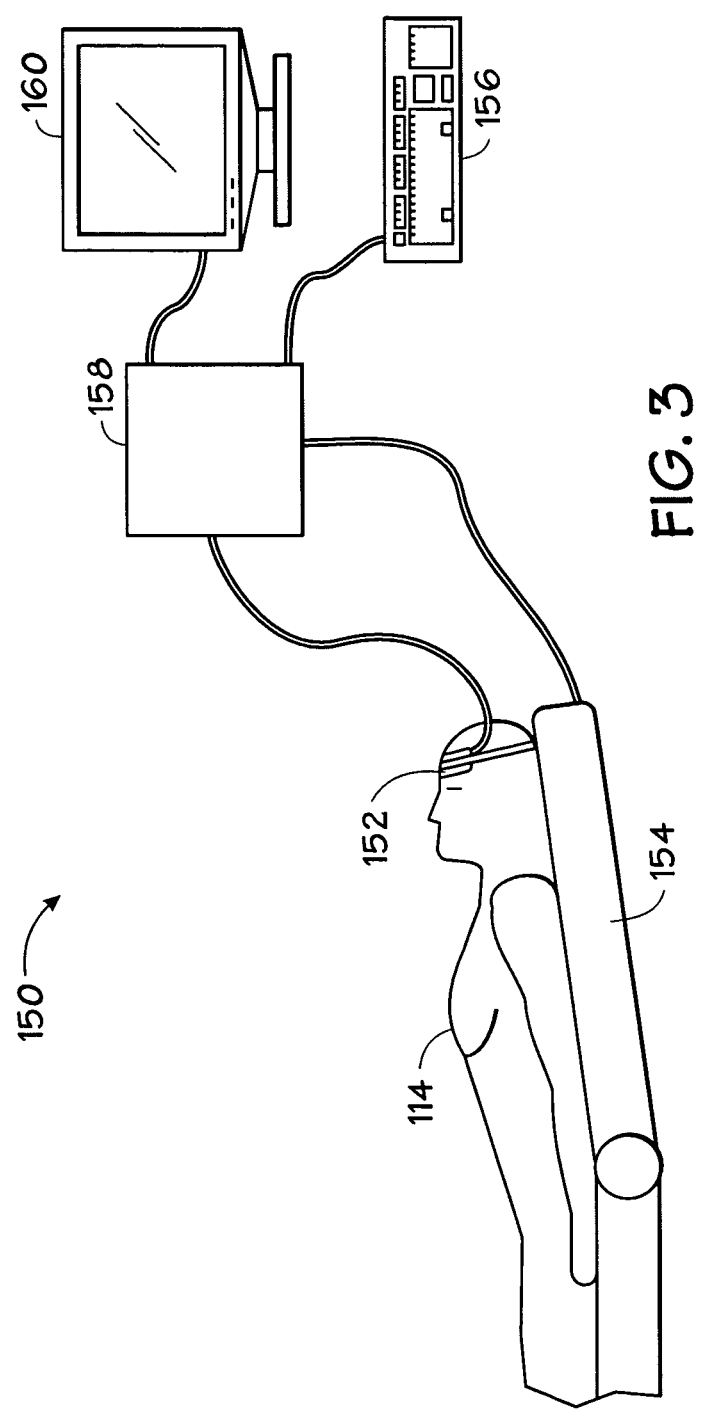
FIG. 3 is a block diagram of an exemplary system for non-invasively monitoring a patient's intracranial pressure in accordance with an exemplary embodiment of the present invention.

FIG. 3 is a block diagram of another system for non-invasively monitoring a patient's ICP in accordance with an exemplary embodiment of the present invention. The system is generally designated by reference number 150. The system 150 includes a pulse sensor 152, an adjustable head elevator 154, an input device 156, a monitor 158, and an output screen 160. The monitor 158 may include a vital signs monitor (e.g., a pulse rate monitor, a pulse oximeter) and/or a pressure mapping device. For example, the monitor 158 may be adapted to receive input from a component of the pulse sensor 152 (e.g., the optical measurement device 16) relating to detecting venous pulsations. Additionally, the monitor may be adapted to receive input from a sensitive pressure measurement device (e.g., the pressure sheet 20) in the pulse sensor 152 that is indicative of pulse. Further, the monitor 158 may be configured to measure a patient's head elevation based on input (e.g., an angle of inclination) from the adjustable head elevator 154. The monitor 158 may utilize correlations between detected venous pulsations and elevation measurements to facilitate estimation of ICP. For example, the adjustable head elevator 154 may be adjusted to elevate the patient's head over the level of the patient's heart until the detected venous pulsations are abolished. The angle of the adjustable head elevator 154 required to abolish the venous pulsations may then be used to calculate an estimated value of the patient's ICP.

Venous pulsations have been observed in pulse measurement data from the forehead. These pulsations are essentially synchronous with the cardiac cycle and occur more frequently under conditions that would elevate venous return from the brain. For example, venous pulsations generally occur more frequently when the head is below the heart or when venous return is restricted during a surgical procedure. Such venous pulsations may be abolished by applying pressure to the patient's forehead. For example, in one embodiment, the headband 102 may be utilized (e.g., tightened or inflated) to apply enough pressure to abolish detected venous pulsations in a patient's forehead. Similarly, as discussed above, the adjustable head elevator 154 may be adjusted to elevate the patient's head over the level of the patient's heart to abolish the venous pulsations as a result of gravity.

It is believed that correlations may be established between venous pulsations in a patient's forehead and the patient's ICP. Such correlations are predicted based in part on how the cardiac cycle affects ICP. The cardiac cycle results in variations in cerebral blood volume. During systole, the net inflow of blood increases intracranial volume, and during diastole, the net outflow of blood decreases the intracranial volume. Because the skull is essentially a rigid container, the increase in intracranial volume caused during systole results in a pressure change. This pressure change sets up a pulse wave in both the low pressure venous blood and CSF. Pulsatile changes in venous volume tend to increase with ICP, because increased ICP generally results in less compliant brain tissue. Thus, to maintain oxygen delivery to the brain, the sympathetic nervous system will increase arterial blood pressure sufficiently to keep the veins open and facilitate blood flow through them. This indicates that, at least until a point of failure, ICP will not exceed venous pressure in the brain.

Blood from the forehead drains into the cavernous sinus inside the skull and eventually drains through the internal jugular. As such, the venous blood from the forehead is in direct communication with that of the brain. Furthermore, there are essentially no valves in these veins. This direct communication and lack of valves suggests that pressure changes associated with the venous blood inside the skull have a direct effect on the blood draining from the forehead. Accordingly, it is likely that venous pulsations observed with the forehead sensor 10, and a pressure or elevation required to overcome the venous pulsations, will correlate with intracranial venous pressure. Further, intracranial venous pressure is affected by elevated ICP. Therefore, the amount of pressure or elevation required to abolish venous pulsations observed with the forehead sensor should correlate to the maximum venous pressure in the brain.

In view of the predictive correlations discussed above, the systems 100 and 150 may detect and abolish venous pulsations in the patient's forehead to estimate ICP. Specifically, the system 100 may measure the amount of pressure or the system 150 may measure the head elevation required to abolish detected venous pulsations in the patient's forehead and then estimate ICP based on correlations between ICP and the measured pressure and/or elevation. For example, in one embodiment, the monitor 108 may calculate an estimate of ICP, or simply determine that an elevated ICP is likely, based on input from the sensor 10, the headband 102 and/or input from a clinician received via the input device 110. In another embodiment, the monitor 158 may calculate an estimate of ICP, or simply determine that an elevated ICP is likely, based on input from the pulse sensor 152, the adjustable head elevator 154, and/or input from a clinician received via the input device 156.

In one embodiment, as illustrated by FIG. 2, the headband 102 may be utilized to facilitate estimation of the patient's ICP. For example, the monitor 108 may receive signals from the sensor 10 that are indicative of venous pulsations. In response, the monitor 108 may cause the headband 102 to gradually inflate and increase pressure on the forehead by initiating the pump 106. The headband 102 may be designed to distribute pressure only on certain portions of the forehead (e.g., above the patient's eyebrows). When the sensor 10 indicates that venous pulsations have ceased, the corresponding pressure measurement may be utilized to estimate ICP. Indeed, the pressure required to abolish the venous pulsations may be essentially equivalent to the ICP. This pressure measurement may be received from a pressure measuring device, such as the pressure sheet 20 or a calibrated device (e.g., an electronic pressure gauge) on the pump 106. The measurements taken during such a process may be displayed on the screen 112 along with the estimate of ICP.

In another embodiment, as illustrated by FIG. 3, the monitor 158 may estimate ICP by adjusting the patient's head elevation. For example, the monitor 158 may receive signals from the pulse sensor 152 that are indicative of venous pulsations. In response, the monitor 158 may cause the adjustable head elevator 154 to raise the patient's head until the venous pulsations are abolished. The angle or level of elevation required to stop the pulsations may be measured and utilized by the monitor 158 along with the correlations based on the effects of gravity on arterial pressure to estimate ICP. Further, the measurements and ICP estimates may be displayed on the screen 160.

It should be noted that in some embodiments, a clinician may control the amount of pressure and/or the patient's head elevation used to stop the venous pulsation by inputting certain pressure or elevation values into the monitor 108 or 158 via the input device 110 or 156 (e.g., a keyboard). Additionally, in some embodiments, a clinician may manually apply pressure to stop detected venous pulsations. For example, a clinician may simply press the sensor 10 with a finger, manually tighten the headband 102, or manually adjust the patient's head elevation until detected venous pulsations are abolished. The monitor 108 or 158 may automatically receive pressure measurements from the sensor 10 or elevation measurements from the adjustable head elevator 154 that correspond to the abolishment of the detected venous pulsations and use these measurements to estimate ICP. Alternatively, the user may manually input measured pressure and elevation values.

Figure 4:
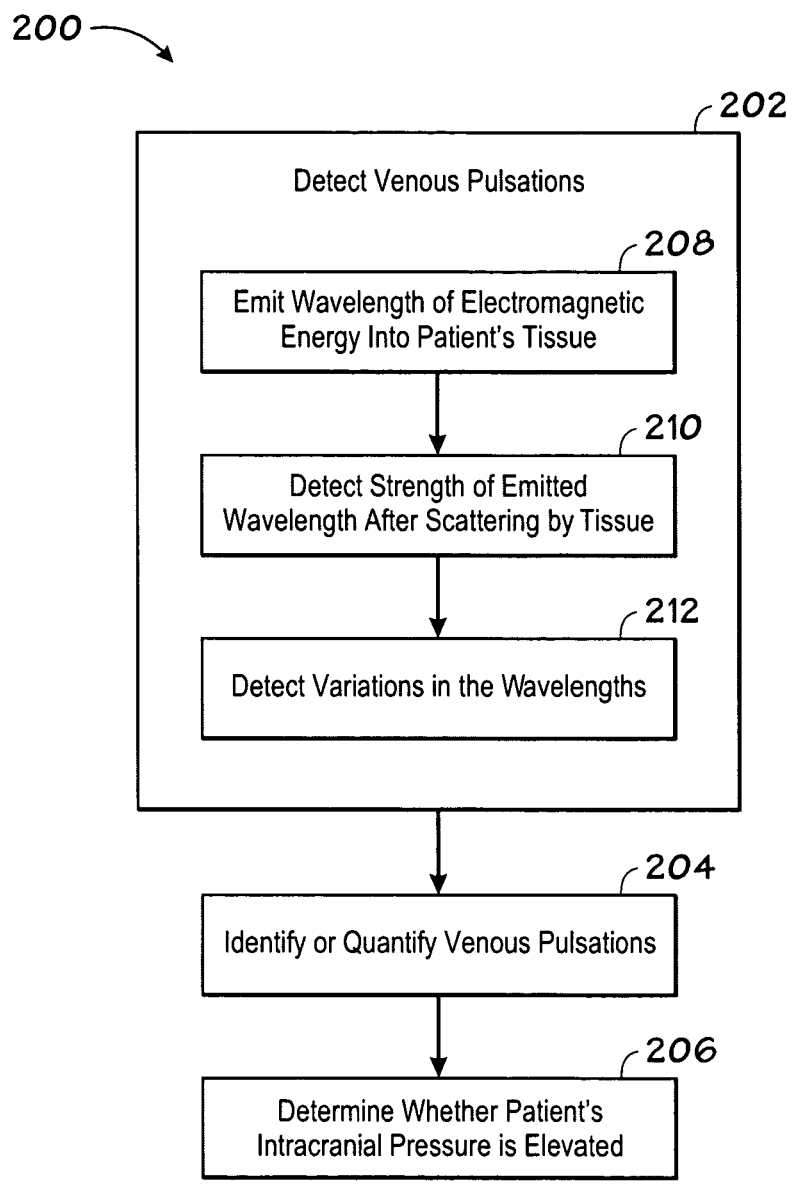
FIG. 4 is a block diagram of an exemplary method for detecting intracranial pressure in accordance with an exemplary embodiment of the present invention.

FIG. 4 is a block diagram of a method for detecting ICP in accordance with an exemplary embodiment of the present invention. The method is generally designated by reference number 200. The method 200 comprises three major acts. Venous pulsations in a patient's forehead are detected (block 202). The venous pulsations are identified and/or quantified (block 204). Whether the patient's ICP is elevated is determined based on correlations between characteristics of the venous pulsations and levels of ICP (Block 206).

Multiple methods may be utilized in block 202 to detect venous pulsations. For example, the methods disclosed in U.S. Patent Publication No. 20050197579 and U.S. application Ser. No. 11/528,295 entitled "Method and Apparatus for Detection of Venous Pulsation," by Clark Baker, filed on Sep. 27, 2006, which are hereby incorporated by reference in their entirety, may be utilized in accordance with embodiments of the present invention. While these various methods may be used, the illustrated embodiment provides a specific example of venous pulsation detection. Indeed, in the illustrated embodiment, the method includes emitting one or more wavelengths of electromagnetic energy (e.g., light) into the patient's forehead tissue (block 208), detecting the strength of the emitted wavelengths after being scattered by the tissue (block 210), and detecting variations in the wavelengths that correspond to the patient's pulse (212). The acts represented by blocks 208, 210, and 212 generally result in detection of venous pulsations in the patient's forehead, if the pulsations are present. In another embodiment, venous pulsations may be detected by comparing an oxygen saturation value computed from oximetry data obtained from a patient's forehead with an oxygen saturation value computed from oximetry data obtained from one of the patient's extremities (i.e. a digit). The veins of the extremities have valves that keep venous blood from backing up and pulsing. Accordingly, an oximetry sensor on the extremity can be presumed to produce values reflective of arterial oxygen saturation, whereas a forehead oximetry sensor can be presumed to produce lower values (i.e., values that are intermediate between arterial and venous oxygen saturation), when venous pulsation occurs at this site. Further, venous pulsations may be detected by analyzing phase differences between signals at the forehead site and an ECG (electrocardiogram) signal.

As set forth above, block 204 represents identifying or quantifying the venous pulsations. This may be achieved by analyzing the variations in the wavelengths detected in block 212. In one embodiment, it is believed that an analysis of the shape of the variations may facilitate identification or quantification of the venous pulsations for correlation with ICP levels. For example, height and width measurements of the wavelengths may be combined with heart rate measurements to establish ICP correlations. In another embodiment, the analysis may include observations relating to phase differences between variations in multiple wavelengths. In yet another embodiment, the analysis may include observations relating to ratios of the variations in multiple wavelengths. For example, wavelengths may be emitted and detected on various parts of the patient's forehead and corresponding variation ratios may be indicative of ICP. Alternatively, it is believed that time and frequency analysis of the venous pulsations, either by themselves or relative to the cardiac cycle, may be used to elucidate ICP information. For example, spectral analysis of decomposed frequency domains or complex algorithms (e.g., geometric measures, non-linear dynamics, power law scaling, detrended fluctuation analysis, or Shannon entropy). It is believed that this type of analysis may be used as an early indicator of patients at risk of developing high ICP.

In accordance with other embodiments of the present invention, the venous pulsations may be quantified by measuring a pressure or an elevation of the patient's head with respect to the patient's heart required to abolish detected venous pulsations. Indeed, such techniques may include applying pressure to the patient's forehead via the sensor or adjusting the patient's upper body to a certain angle to abolish detected venous pulsations. For example, a clinician may block venous pulsations by simply pressing on the sensor or by tightening a headband on the patient's forehead. Pressure measurements between the sensor and the patient may be taken to determine how much pressure was required to overcome the venous pulsations. Specifically, a pressure sheet sensor (e.g., pressure sheet 20) may be utilized to determine the pressure required to abolish the venous pulsations, and the value of the pressure may be utilized with a predicted correlation to estimate ICP.

The pressure required to abolish the venous pulsations correlates with ICP because the supraorbital vein on the forehead is in direct communication with the superior ophthalmic vein, which is a tributary to the cavernous sinus (inside the cranial vault). As there are no valves in any of these veins, pressures can be directly transmitted from the cavernous sinus to the supraorbital vein. Indeed, Poiseuille's law states that blood flows within a vessel from point A to point B if there is an intravascular pressure gradient between the two points. As such, pressure differences between the cavernous sinus and the supraorbital pressure will result in a volume flow correlating with the pressure gradient. As previously mentioned, the cardiac cycle results in a rhythmic influx of arterial blood into the cranial vault, and a corresponding pulsatile efflux of the low pressure fluids (venous and cerebral spinal fluid) to minimize any net change in intra-cranial pressure. These venous pulsations can be monitored to provide information regarding intracranial pulse pressure and the corresponding pressure in the CSF (clinical intra-cranial pressure). It should further be noted that as the superior ophthalmic vein enters the crania vault, it passes through the subarachnoid space (the compartment containing the CSF). As the walls of veins lack rigidity, elevations in ICP will eventually result in occlusions of this segment of the vein and will abolish any venous pulsations transmitted to the supraorbital vein in the forehead. This occurs in the clinically important region of 20-25 mmHg, and could therefore be used as an indicator of when to treat.

In another example, the patient's upper body may be adjusted to an angle such that the patient's head is a certain distance above the patient's heart. This distance or the angle of the patient's body required to stop the venous pulsations may be measured and used with a predicted correlation to estimate ICP. Similar to the description set forth above, altering the volume in the cranial vault will result in associated changes in the venous pulsations of the supraorbital vein. In this case, gravity may be used to change the volume of blood and CSF in the cranial vault, which in turn may have a predictable effect on the venous pulsation.

As set forth above, block 206 represents determining whether the patient's ICP is elevated based on correlations between characteristics of the venous pulsations and levels of ICP. For example, it is anticipated that if the pressure required to abolish venous pulsation exceeds a predetermined value, such as 20 mmHg, the patient will have an elevated ICP. Similarly, it is anticipated that direct correlations between certain elevations of the patient's head above the patient's heart will indicate that the patient has an elevated ICP. Further, it is anticipated that in some embodiments, an elevated ICP will be discernable from features of the signals relating to venous pulsations. Upon detecting an elevated ICP, embodiments of the present invention may initiate an alarm or automatically deliver pharmaceuticals to the patient to relieve the elevated ICP.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method for monitoring intracranial pressure, comprising:
   using a sensor:
   emitting at least one electromagnetic wavelength into forehead tissue of a patient; and
   detecting characteristics of the at least one electromagnetic wavelength after the at least one electromagnetic wavelength has been scattered by the tissue, wherein the characteristics include variations in the at least one electromagnetic wavelength corresponding to a pulse; and
   using a monitor:
   analyzing the variations to identify venous pulsations; and
   determining whether intracranial pressure is elevated in the patient based on a correlation only between the venous pulsations and levels of intracranial pressure.

2. The method of claim 1, comprising:
   applying an increasing amount of pressure to the forehead tissue until the venous pulsations are abolished;
   measuring the amount of pressure corresponding to abolishment of the venous pulsations; and
   quantifying the intracranial pressure based on the measured amount of pressure.

3. The method of claim 1, comprising:
   elevating the forehead tissue relative to the heart of the patient until the venous pulsations are abolished;
   measuring the elevation corresponding to abolishment of the venous pulsations; and
   quantifying the intracranial pressure based on the measured elevation.

4. The method of claim 1, comprising analyzing a shape of the variations to identify the venous pulsations based on a correlation between the shape and the venous pulsations.

5. The method of claim 1, comprising analyzing a phase difference between variations in at least two electromagnetic wavelengths to identify the venous pulsations based on a correlation between the phase difference and the venous pulsations.

6. The method of claim 1, comprising:
   emitting a first electromagnetic wavelength into a first portion of the forehead tissue of the patient;
   emitting a second electromagnetic wavelength into a different portion of the forehead tissue of the patient; and
   comparing a ratio of the variations in the first electromagnetic wavelength and the variations in the second electromagnetic wavelength to identify the venous pulsations based on a correlation between the ratio and the venous pulsations.

7. The method of claim 1, comprising identifying the venous pulsations by comparing a first oxygen saturation estimate obtained from the forehead tissue and a second oxygen saturation estimate from a different portion of the forehead tissue.

8. The method of claim 1, comprising delivering a pharmaceutical to the patient to control elevated intracranial pressure when elevated intracranial pressure is determined to be present.

9. The method of claim 1, comprising comparing saturation values from multiple sites or comparing phase differences between a pulse and an ECG to identify the venous pulsations.

10. A system for monitoring intracranial pressure, comprising:
    a sensor comprising:
      an emitter configured to emit at least one electromagnetic wavelength into tissue of a patient; and
      a detector configured to detect the at least one electromagnetic wavelength after scattering by the tissue;
    a monitor configured to be in electronic communication with the sensor, the monitor configured to analyze characteristics of the at least one detected electromagnetic wavelength to identify venous pulsations and to determine whether intracranial pressure is elevated in the patient based on a correlation only between the venous pulsations and levels of intracranial pressure; and
    an adjustment measurement device configured to measure a level of adjustment corresponding to abolishment of identified venous pulsations.

11. The system of claim 10, comprising:
    an inflatable headband; and
    a pump configured to inflate the headband to increase pressure between the sensor and the tissue.

12. The system of claim 10, comprising an adjustable head elevator configured to elevate the tissue with respect to the heart of the patient.

13. The system of claim 10, wherein the monitor comprises a pressure mapping system.

14. The system of claim 10, wherein the monitor comprises a pulse oximeter.

15. A method, comprising:
    directing a sensor to emit at least one electromagnetic wavelength into tissue of a patient;
    determining whether venous pulsations are present in the tissue based on the received sensor signal;
    if venous pulsations are present, adjusting an adjustment measurement device until venous pulsations cease; and
    determining whether intracranial pressure is elevated in the patient based on a correlation only between the level at which venous pulsations cease and a level of intracranial pressure.

16. The method of claim 15, wherein the adjustment measurement device is configured to measure an amount of pressure applied to the sensor.

17. The method of claim 15, wherein the adjustment measurement device comprises a pressure sheet.

18. The method of claim 15, wherein the adjustment measurement device is configured to measure an elevation relative to the heart of the patient.

* * * * *